United States Patent [19]

Klaenhammer et al.

[11] Patent Number: 5,593,885
[45] Date of Patent: Jan. 14, 1997

[54] PHAGE DEFENSE ROTATION STRATEGY

[75] Inventors: Todd R. Klaenhammer, Raleigh, N.C.; Wesley D. Sing, Indianapolis, Ind.; Colin J. Hill, Cork, Ireland

[73] Assignee: North Carolina State University, Raleigh, N.C.

[21] Appl. No.: 375,072

[22] Filed: Jan. 18, 1995

Related U.S. Application Data

[63] Continuation of Ser. No. 117,550, Sep. 7, 1993, abandoned, which is a continuation of Ser. No. 987,054, Dec. 7, 1992, abandoned, which is a continuation of Ser. No. 578,660, Sep. 5, 1990, abandoned.

[51] Int. Cl.⁶ .............................. C12N 1/20; C12N 1/21
[52] U.S. Cl. ..................... 435/252.3; 435/253.4; 435/252.4
[58] Field of Search ...................... 435/252.3, 253.4, 435/252.4

[56] References Cited

U.S. PATENT DOCUMENTS 4,883,756  11/1989  Klaenhammer et al. ............ 435/252.3
4,931,396   6/1990  Klaenhammer et al. ............ 435/320.1

OTHER PUBLICATIONS

R. R. Hull; *Control of Bacteriophage in Cheese Factories*, The Australian Journal of Dairy Technology pp. 65–66 (Jun. 1977).

S. Lofdahl et al; *Cloning of Restriction Fragments of DNA from Staphylococcal Bacteriophage φ11*, J. Virol 37 pp. 795–801 (1981).

R. J. Ericksson; *Bacteriophage problems in the dairy industry*, Y. Industries International (Mar. 1980).

G. H. Richardson et al; *Defined Single Strains of Lactic Streptococci in Bulk Culture for Cheddar and Monterey Cheese Manufacture*, Dairy Sci. 63 1981–1986 (1980).

M. E. Sanders; *Phage resistance in lactic acid bacteria*, Biochimie 70, pp. 411–421 (1988).

Klaenhammer et al. (1987) FEMS Microbiol. Rev. vol. 46 (3), 313–325.

Erickson (1980), Dairy Industries International, vol. 45, Abstract only.

Sing et al. (1986), Applied Environmental Micro., vol. 51, pp. 1264–1271.

Genetic Characterization of Multple Mechanisms of Phage Defense from a Prototype Phage–Insensitive Strain, Lactococcus lactis ME2[1], 1989 J Dairy Sci, 72:3429–3443; Todd R. Klaenhammer.

Starters: Application In the Dairy; Milk –The Vital Force, 95–103; 1987 by D. Reidel Publishing Company; Charles Daly, Cork Ireland.

Interactions of Bacteriophages with Lactic Streptococci[1], Todd R. Klaenhammer; Advances in Applied Microbiology, vol. 30; pp. 1–29.

Progress in Dairy Starter Culture Technology, Alan R. Huggins; Jun. 1984 Food Technology; pp. 41–50.

Bacteriophage in Cheese Manufacture, H. R. Whitehead and G. J. E. Hunter; J. Dairy Res. 15 1947; 112–120.

Reviews Of The Progress of Dairy Science: Cheese Starters; R. C. Lawrence, T. D. Thomas and B. E. Terzaghi; Journal of Dairy Research 1976, pp. 141–193.

Symposium: Research and Development Trends in Natural Cheese Manufacturing and Ripening; R. C. Lawrence et al.; 1978 J Dairy Science; pp. 1181–1191.

Phage–Insensitive, Multiple–Strain Approach to Cheddar Cheese Making*a*, R. K. Thunell and W. E. Sandine; 1981 J Dairy Science; 2270–2277.

Bacteriophage in Cheese Manufacture; H. R. Whitehead; The Dairy Research Institute, Palmerston North, New Zealand; Bacteriological Reviews 17, pp. 109–123 (1953).

Robert J. Erickson, *Dairy Industrial International* 45, 37–44 (1980).

*Primary Examiner*—George C. Elliott
*Attorney, Agent, or Firm*—Bell, Seltzer, Park & Gibson

[57] ABSTRACT

A phage defense rotation strategy for use in the successive fermentations of a substrate in a fermentation plant is disclosed. The strategy comprises (a) fermenting substrate with a first bacterial culture comprising a bacterial strain capable of fermenting the substrate and, preferably, carrying a first phage defense mechanism; and then (b) fermenting the substrate with a second bacterial culture comprising a second bacterial strain isogenic with the first bacterial strain, wherein the second strain carries a second phage defense mechanism different from the first phage defense mechanism.

Also disclosed is a mixed bacterial culture capable of fermenting a substrate. The mixed culture comprises (a) a first bacterial strain carrying a first phage defense mechanism; and (b) a second bacterial strain isogenic with the first strain, wherein the second strain carries a phage defense mechanism different from the phage defense mechanism carried by the first strain.

44 Claims, 3 Drawing Sheets

PHAGE DEFENSE ROTATION STRATEGY

This is a continuation of application Ser. No. 08/117,550 filed on 07 Sep. 1993, abandoned, which is a File Wrapper Continuation of Ser. No. 07/987,054, filed 07 Dec. 1992 now abandoned and which was a File Wrapper Continuation of Ser. No. 07/578,660, filed on 05 Sep. 1990 now abandoned.

FIELD OF THE INVENTION

The present invention relates to fermentation in general, and particularly relates to means for rendering fermentations phage resistant through the rotation of starter cultures.

BACKGROUND OF THE INVENTION

Traditional starter culture programs have depended on phage defense rotation strategies (PDRS) to minimize failures due to bacteriophage attack. See generally T. Klaenhammer, *Advances in Applied Microbiology* 30, 1 (1984); R. Lawrence et al., *J. Dairy Res.* 43, 141 (1976); H. Whitehead and G. Hunter, *J. Dairy Res.* 15, 112 (1947). When lytic phage appear in whey samples during defined single strain rotations, a replacement strain which is ideally phage-unrelated is incorporated into the rotation. History has proven, however, that it is difficult to identify sufficient numbers of phage-unrelated strains to run complex rotation programs. Secondly, few strains are available that remain insensitive long enough to make their introduction into factories worthwhile. See, e.g., A. Huggins, *Food Technol.* (June 1984).

There are additional problems with traditional starter culture rotation strategies. Although some stains are not attacked by existing phages when introduced, phage may eventually appear due to phage mutation, modification, and build-up. See H. Heap and R. Lawrence, *N.Z.J. Dairy Sci. Technol.* 11, 16 (1976); G. Limsowtin and B. Terzaghi, *N.Z.J. Dairy Sci. Technol.* 11, 251 (1976); L. Pearce, *N.Z.J. Dairy Sci. Technol.* 13, 166 (1978); M. Sanders and T. Klaenhammer, *Appl. Environ. Microbiol.* 40, 500 (1980). Moreover, in many cases, the longevity and starter activity of complex strain rotations is unpredictable and often leads to early failure. See, e.g., G. Limsowtin et al., *N.Z.J. Dairy Sci. Technol.* 13, 1 (1977); R. Thunell et al., *J. Dairy Sci.* 64, 2270 (1981). Furthermore, prolonged rotations involving numerous strains increase the level and diversity of phage contaminating the plant. Seek e.g., H. Heap and R. Lawrence, *N.Z.J. Dairy Sci. Technol.* 12, 213 (1981); R. Lawrence et al., *J. Dairy Sci.* 61, 1181 (1978); R. Thunell et al., *J. Dairy Sci.* 64, 2270 (1981).

Studies on phage-insensitive strains of *lactococci* have uncovered the genetic basis for a variety of different phage defense mechanisms. See T. Klaenhammer, *FEMS Microbiol. Rev.* 46, 313 (1987); M. Sanders, *Biochemie* 70, 411 (1988). Such phage defense mechanisms include prevention of adsorption (Ads), restriction and modification (R/M), and abortive infection (Hsp). Development of gene transfer systems in bacteria, such as conjugation, transformation, and electroporation, have provided the opportunity to construct strains with improved characteristics. The existence of conjugal transfer ($Tra^+$) and phage resistance (Hsp or R/M) determinants on plasmids such as pTR2030 ($Tra^+$, $Hsp^+$, $R^+/M^+$), pTN20 ($Tra^+$, $R^+/M^+$), and pAJ1106 ($Tra^+$, $Hsp^+$) facilitates construction of phage-resistant starter strains using simple conjugal strategies which are acceptable as a natural means by which to genetically manipulate food grade microorganisms. D. Higgins et al., *J. Bacteriol.* 170, 3435 (1988); A. Jarvis et al., *Appl. Environ. Microbiol.* 55, 1537 (1989); M. Sanders et al., *Appl. Environ. Microbiol.* 52, 1001 (1986); W. Sing and T. Klaenhammer, *Appl. Environ. Microbiol.* 51, 1264 (1986). When employed repeatedly in the field, transconjugants carrying pTR2030 (Hsp+) have survived prolonged use in milk fermentations. See M. Sanders, *Biochemie* 70, 411 (1988). However, phage resistant to the Hsp mechanism have been detected, and pose a viable threat to prolonged use of a single $Hsp^+$ strain in rotation.

With neither traditional phage rotation strategies nor more recent genetic strategies providing a complete solution to the problem of phage infection of culture media, their is an ongoing need for new means for combating phage infections in the fermentation industry. The present invention is based on our ongoing research in this field.

SUMMARY OF THE INVENTION

A first aspect of the present invention is a phage defense rotation strategy for use in the successive fermentations of a substrate in a fermentation plant. The method comprises (a) fermenting substrate with a first bacterial culture comprising a bacterial strain capable of fermenting the substrate and, preferably, carrying a first phage defense mechanism; and then (b) fermenting the substrate with a second bacterial culture comprising a second bacterial strain isogenic with the first bacterial strain, wherein the second strain carries a second phage defense mechanism different from the first phage defense mechanism.

The method may be carried out with more than two isogenic strains. Thus, for example, the process described above may be continued by (c) fermenting the substrate with a third bacterial culture comprising a bacterial strain isogenic with said first and second strains, wherein the third strain carries a phage defense mechanism different from the first and second phage defense mechanisms.

The fermenting steps of the foregoing process may be followed by repeating previous steps or by cyclically repeating the steps. These methods are particularly advantageous when the substrate is susceptible to infection by phage, e.g., where the substrate is nonsterile, and/or where the fermentation is carried out under nonsterile conditions.

A second aspect of the present invention is a mixed bacterial culture capable of fermenting a substrate. The mixed culture comprises (a) a first bacterial strain carrying a first phage defense mechanism; and (b) a second bacterial strain isogenic with the first strain, wherein the second strain carries a phage defense mechanism different from the phage defense mechanism carried by the first strain. The culture may contain additional isogenic strains, for example a third bacterial strain isogenic with the first and second strains, wherein the third strain carries a phage defense mechanism different from the phage defense mechanisms carried by the first and second strains. Otherwise, the culture may be either a pure culture free of non-isogenic strains, or a mixed culture containing non-isogenic strains.

A third aspect of the present invention is a set of bacterial cultures useful for carrying out a PDRS as described above, or making mixed bacterial cultures as described above. The set comprises (a) a first bacterial culture comprising a first bacterial strain carrying a first phage defense mechanism; and (b) a second bacterial culture comprising a second bacterial strain isogenic with the first strain, wherein the second strain carries a phage defense mechanism different from the phage defense mechanism carried by the first strain.

The phage defense rotation strategy (PDRS) and mixed cultures described herein provide innovative starter rotation and cultural practices. Phage development is not controlled by altering phage-host specificity or use of resistant mutants, as in traditional techniques. See, e.g., A. Huggins and W. Sandine, *J. Dairy Sci.* 62, 70 (1979); R. Hull, *Aust. J. Dairy Technol.* 32, 65 (1977); A. Jarvis, *Appl. Environ. Microbiol* 54, 777 (1988); R. Marshall and N. Berridge, *J. Dairy Res.* 43, 449 (1976). The strategic use of different mechanism types and specificities enables one to control unpredictable phage populations which exist in the fermentation environment. This approach to starter protection allows the use of a single isogenic strain over a prolonged rotation period. Delivery of these same phage defense mechanisms into a second or third host background can provide favorable protection against phages homologous for that host. In the future, superior and desirable strains which perform consistently and efficiently in the industry can now be protected using a defense rotation strategy or mixed isogenic culture in conjunction with single or multiple mechanisms carried by each host.

BRIEF DESCRIPTION OF THE DRAWINGS

FIG. 3A: Initial titer of $\phi$48=10$^2$ PFU/ml; whey only added after the first cycle. FIG. 3B: Initial titer of $\phi$48=10$^3$ PFU/ml; whey only added after the first cycle.

DETAILED DESCRIPTION OF THE INVENTION

Figure 1A:
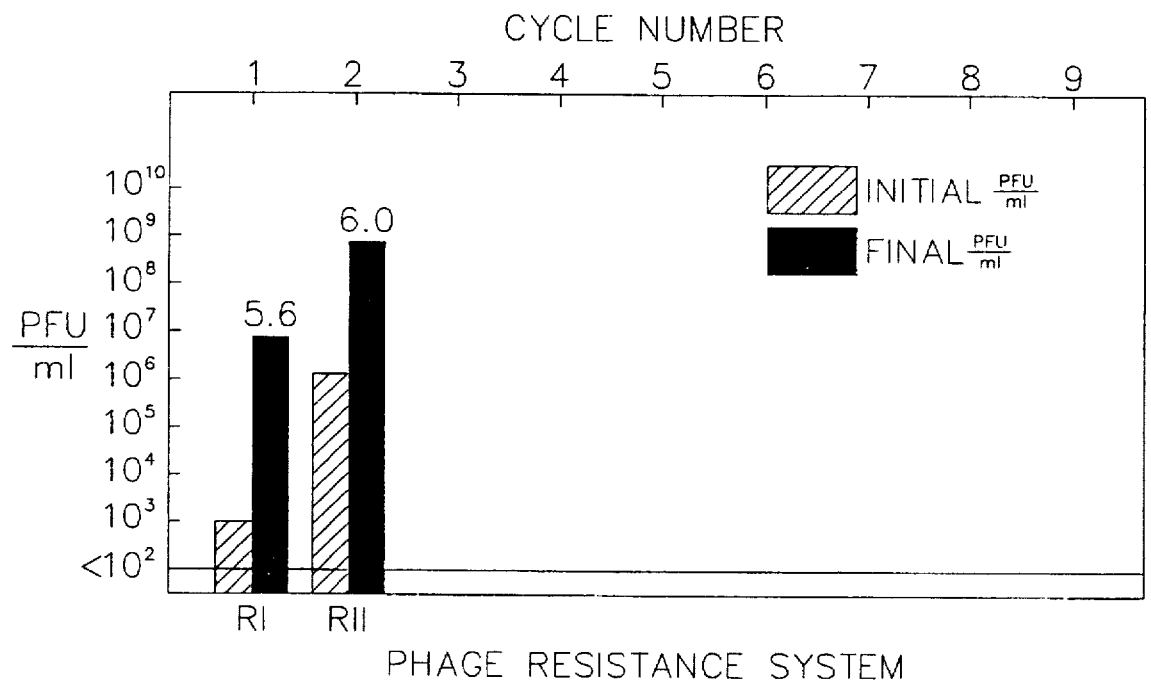
FIGS. 1A and 1B show, for Rotation Sequence B, the effect of *L. lactis* NCK204 (pTR2030; Hsp$^+$, R$^+$/M$^+$) on phage development during starter culture activity tests. Initial phage $\phi$31 titer=10$^6$ PFU/ml; whey only added after the first cycle. RI=NCK347 (pTN20), RII=NCK346 (pTRK11), H=NCK204 (pTR2030). Final pH is indicated on top of the bar representing final PFU/ml.

The term "isogenic" as used herein to compare two or more bacterial strains refers to bacterial strains which (a) are derived from the same parental strain as one another, (b) have essentially the same capability of fermenting substrates as one another; and (c) have the same bacteriophage binding characteristics as one another (i.e., phage which binds to the surface of one bind to the surface of the other(s), and phage which does not bind to the surface of one does not bind to the surface of the other(s)).

A feature of sets of isogenic strains of bacteria disclosed herein is that they differ in at least one bacteriophage defense mechanism carried thereby. Isogenic strains may carry more than one phage defense mechanism, and these additional defense mechanisms may be the same or different, so long as each strain differs from the other in at least one phage defense mechanism. Phage defense mechanisms incorporated into various strains need not, of course, be operable in all phage environments, as many, if not most, phage defense mechanisms are ineffective in protecting bacteria against some species of phage.

A. PHAGE DEFENSE MECHANISMS

Numerous phage defense mechanisms are known which may be employed in practicing the present invention, including prevention of adsorption (Ads), restriction and modification (R/M), and abortive infection (Hsp). See generally A. Baumgartner et al., 35 FEMS Microbiol. Lett. 233 (1986); J. Boussemaer et al., 47 J. Dairy Res. 401 (1980); A. Chopin et al., 11 Plasmid 260 (1984); W. deVos et al., 23 FEMS Microbiol. Letters 175 (1984); B. Froseth et al., 71 J. Dairy Sci. 275 (1988); M. Gautier and M.-C. Chopin, 53 Appl. Environ. Microbiol. 923 (1987); D. Higgins et al., 170 J. Bacteriol. 3435 (1988); C. Hill et al., 55 Appl. Environ. Microbiol. 1684 (1989); A. Jarvis 54 Appl. Environ. Microbiol. 777 (1988); A. Jarvis et al., 55 Appl. Environ. Microbiol. 1537 (1989); T. Klaenhammer and R. Sanozky, 131 J. Gen. Microbiol. 1531 (1985); N. Laible et al., 70 J. Dairy Sci. 2211 (1987); L. McKay and K. Baldwin, 47 Appl. Environ. Microbiol. 68 (1984); C. Murphy et al., 54 Appl. Environ. Microbiol. 1951 (1988); M. Sanders and T. Klaenhammer, 46 Appl. Environ. Microbiol. 1125 (1983); M. Sanders and T. Klaenhammer, 47 Appl. Environ. Microbiol. 979 (1984); W. Sing and T. Klaenhammer, 51 Appl. Environ. Microbiol. 1264 (1986); L. Steenson. and T. Klaenhammer, 50 Appl. Environ. Microbiol. 851 (1985); L. Steenson and T. Klaenhammer, 69 J. Dairy Sci. 2227 (1986).

The phage defense mechanisms used to carry out the present invention may be carried by a plasmid. In some cases, genes encoding R/M and Hsp exist on different plasmids or on the same plasmid and, in either case, provide multiple types of defense. In other cases, multiple R/M systems exist within a single strain and exhibit elevated levels of phage restriction.

An abortive phage defense mechanism useful for carrying out the present invention is one carried by a plasmid selected from the group consisting of (a) the plasmid pTR2030, which encodes phage resistance phenotype and conjugal transfer phenotype upon expression in *lactococci* (the *lactococci* previously referred to as group N *streptococci*), and (b) a derivative of pTR2030, the derivative encoding the phage resistance phenotype encoded by the plasmid pTR2030 upon expression in *lactococci*. These plasmids are disclosed in commonly owned U.S. Pat. No. 4,931,396 to Klaenhammer et al. issued Jun. 5, 1990, the disclosure of which applicant specifically intends to be incorporated herein by reference.

Phage encoded resistance (Per) is also useful for practicing the present invention. Per is unique among bacterial genotypes since it is derived from the genome of the bacteriophage itself. A bacterial cell which carries Per comprises a bacterial cell containing a bacteriophage origin of replication (ori) operatively associated with a DNA sequence incapable of producing live bacteriophage. The bacterial cell is capable of being infected by a bacteriophage, the DNA of which, once injected into the bacterial cell, competes with Per for binding to DNA polymerase.

Bacterial cells containing Per can be made by (a) conducting a fermentation of a substrate in a medium containing a defined bacterial culture until bacteriophage are detected in the medium, the bacteriophage being specific to at least one bacteria in the medium; (b) isolating the bacteriophage; (c) digesting DNA of the bacteriophage to produce a library of DNA fragments; (d) transforming the bacteria susceptible to said bacteriophage with the library of DNA fragments to provide transformed bacteria; (e) selecting from among the recombinant bacteria, a bacteriophage-resistant transformed bacteria; (f) adding bacteriophage resistant recombinant bacteria to the medium; and (g) recommencing step (a). When the library of DNA fragments is made, they must be joined to heterologous DNA which is incapable of coding for the phage from which the fragments are derived. In a preferred embodiment of the present invention, the DNA library is made by first inserting the fragments of the library into a plasmid vector, transforming the bacteria susceptible to the bacteriophage with the plasmid vector, and then propagating the transformed bacteria. Bacteriophage resistant bacteria are selected from among the transformed bacteria by standard screening procedures.

A preferred bacteria carrying Per is *Lactococcus lactis* subsp. *lactis* NCK298, which has been deposited at the American Type Culture Collection, 12301 Parklawn Drive, Rockville, Md. 20852 USA, in accordance with the provisions of the Budapest Treaty, on Aug. 10, 1990, and given ATCC Accession Number 68379. NCK298 contains plasmids pTRK104 and pTRK2030 (the lattter conjugally introduced). The plasmid pTRK104 imparts Per to NCK298, and was made by the procedures described above. pTRK104 is an *E. coli* plasmid containing a 1.4-kb region isolated from the genome of bacteriophage nck202.50 ($\phi$50). The 1.4-kb insert contains the ori of $\phi$50. NCK298, which contains both pTR2030 and pTRK104, is insensitive to contaminating levels of bacteriophages representing both Per-resistant ($\phi$31) and Hsp-resistant ($\phi$50) groups. Thus, Hsp+ and Per+ can work in concert to provide a more extensive range of insensitivity than either mechanism used in isolation. Plasmid pTRK104 can be easily isolated from *L. lactis* NCK298 by lysing the cells via the procedure of Anderson, D. A., and McKay, L. L., *Appl. Environ. Microbiol.* 46: 549–552 (1983). Plasmid pTRK104 can be visualized among the other resident plasmids in NCK298 after electrophoretic migration of the DNA sample in agarose gels; or isolated in pure form by transformation into competent cells of *E. coli* and selection for $Cm^r$ transformants via standard protocols. See Hill, c. et al., *Appl. Environ. Microbiol.* 55: 1684–1686.

Phage defense mechanisms may be transferred into the strain desired for the fermentation by any suitable means, including protoplast transformation, electrotransformation, and conjugal transfer. See generally J. Luchansky et al., 2 Molecular Microbiol. 637 (1988); I. Powell et al., 54 Appl. Environ. Microbiol. 655 (1988); J. Kondo and L. McKay, 43 Appl. Environ. Microbiol. 1213 (1982); J. Kondo. and L. McKay, 48 Appl. Environ. Microbiol. 252 (1984); L. McKay et al., 40 Appl. Environ. Microbiol. 84 (1980).

B. ROTATION STRATEGIES

The phage defense rotation strategy of the present invention may be used in the same manner and under the same circumstances as any conventional phage defense rotation strategy. In general, the phage defense rotation strategy is used in a fermentation plant or facility for the purpose of avoiding phage attack of fermentations, or re-establishing a fermentation after phage attack has occurred. In the phage defense rotation strategy, strains are successively substituted or replaced with a different isogenic strain carrying a different phage defense mechanism. Typically, the substrate to be fermented will originate from the same feedstock or storage vessel, providing the same phage environment during successive fermentations. The PDRS may be used in successive fermentations carried out in the same or different fermentation vessel. For example, in a cheese fermentation plant there may be a plurality of fermentation vessels, some or all of which may be in use, with the plurality of vessels containing the same or different bacterial cultures, and with successive fermentations being carried out in different vessels.

In an embodiment of the invention, the same defense may be present in successive or alternate cycles. For example, a fermentation might be carried out with NCK (R/MI), then with NCK (R/MI and R/MII), then with NCK (R/MI and Hsp).

In another embodiment of the present invention, a multiple strain culture composed of one or more isogenic strains carrying different phage defense mechanisms could be used continuously. In this situation, strain rotation can take two forms. One can rotate to a new multiple strain culture at intervals dictated by factors such as time or performance. Alternatively, one or more strains in the original composite could be removed and replaced by a new isogenic strain carrying one or more different phage defense mechanisms. For example, fermentation might first be carried out with a first culture comprised of NCK (R/MI), NCK (R/MII) and NCK (Hsp). One option for rotation would then be to replace the first culture with a second culture comprised of NCK (R/MIII), NCK (R/MIV) and NCK (HSPII and Per). An alternate option would be to replace one strain in the culture and carry out fermentation with a second culture comprised of NCK (R/MI), NCK (R/MII), and NCK (HSPII and Per).

The timing of rotation can be variable. For example, one multiple strain culture could be used repeatedly for weeks or months before the replacement cycle (new strains) is initiated. The rotation of isogenic strains carrying different phage defense mechanisms can occur as needed or desired, vat-to-vat, day-to-day, month-to-month, or year-to-year depending on other conditions of the process. The choice of timing of rotation is a routine matter to those skilled in the art, and can be made arbitrarily, based on empirical studies, or based on ongoing phage monitoring programs.

Fermentation vessels used to prepare the starter cultures or conduct the process of the present invention depend upon the stage of the fermentation and the substrate or media being fermented. Suitable vessels include both sealed sterile vessels, closed bulk culture vessels, and open, nonsterile vessels or fermentation vats. The instant invention is particularly suitable for us in fermentations carried out under nonsterile conditions where phage infection is more likely.

C. FERMENTATIVE MICROORGANISMS

While the present invention is, in a preferred embodiment, directed to the fermentation of food, the invention may be practiced with any fermentation process susceptible to disruption by bacteriophage infection, including processes for the production of antibiotics, amino acids, and solvents. Products produced by fermentation which are known to have encountered bacteriophage infection, and the corresponding infected fermentation bacteria, include Cheddar and cottage cheese (*Lactococcus lactis, Lactococcus cremoris*), Yogurt (*Lactobacillus bulgaricus, Streptococcus thermophilus*), Swiss cheese (*S. thermophilus, Lactobacillus lactis, Lactobacillus helveticus*), Blue cheese (*Leuconostoc cremoris*), Italian cheese (*L. bulgaricus, S. thermophilus*), Viili (*Lactococcus cremoris, Lactococcus lactis* subsp. *diacetylactis, Leuconostoc cremoris*), Yakult (*lactobacillus casei*), casein (*Lactococcus cremoris*), Natto (*Bacillus subtilis* var. *natto*), Wine (*Leuconostoc oenos*), Sake (*Leuconostoc mesenteroides*), Polymyxin (*Bacillus polymyxa*), Colistin (*Bacillus colistrium*), Bacitracin (*Bacillus licheniformis*), L-Glutamic acid (*Brevibacterium lactofermentum*, *Microbacterium ammoniaphilum*), and acetone and butanol (*Colstridium acetobutylicum*, *Clostridium saccharoperbutylacetonicum*). See generally M. Sanders, Bacteriophages of Industrial Importance, in PHAGE ECOLOGY, 211-44 (S. Goyal, C. Berba and G. Bitton eds. 1987). Thus, the present invention may, for example, be employed in a fermentation process for producing any of the foregoing products with the foregoing bacteria in the manner described herein.

Bacteria capable of fermenting foods include those bacteria used in any type of food fermentation, including, but not limited to, the fermentation of milk, egg, meat, fruit, vegetables, and cereals. See generally Food Biotechnology, (D. Knorr Ed. 1987)(Marcel Dekker, Inc.); Fermented Foods (A. Rose Ed. 1982)(Academic Press); C. Pederson, Microbiology of Fermented Foods, (2d ed. 1979)(AVI Publishing Co.).

Milk is fermented to produce products such as cheese, yoghurt, kefir, and acidophilus milk. Cheese fermentation bacteria are discussed separately below. Otherwise, bacteria used for the fermentation of milk include, but are not limited to, *Lactobacillus bulgaricus*, *Lactobacillus acidophilus*, *Streptococcus thermophilus*, and mixtures thereof. See Food Biotechnology, 530 (D. Knorr Ed. 1987); C. Pederson, Microbiology of Fermented Foods, 105-35 (2d ed. 1979).

Bacteria used for the fermentation of milk to produce cheese include, but are not limited to, *Lactobacillus bulgaricus*, *Lactobacillus helveticus*, *Streptococcus thermophilus*, *Lactococcus lactis*, *Lactococcus cremoris*, *Lactococcus lactis* subsp. *diacetylactis*, and mixtures thereof. See Food Biotechnology, 530 (D. Knorr Ed. 1987); C. Pederson, Microbiology of Fermented Foods, 135-51 (2d ed. 1979).

Bacteria used for the fermentation of egg include *Pediococcus cerevisiae*, *Lactobacillus plantarum*, and mixtures thereof. See Food Biotechnology, 538-39 (D. Knorr Ed. 1987).

Bacteria used for the fermentation of meat (including beef, pork, and poultry) include, but are not limited to, Lactic acid bacteria, *Pediococcus cerevisiae*, *Lactobacillus plantarum*, *Lactobacillus brevis*, *Micrococcus species*, *Leuconostoc citrovorum*, and mixtures thereof. See Food Biotechnology, 538-39 (D. Knorr Ed. 1987); C. Pederson, Microbiology of Fermented Foods, 210-34 (2d ed. 1979); U.S. Pat. No. 2,225,783 to Jensen and Paddock.

Bacteria used for the fermentation of vegetables (e.g., carrots cucumbers, tomatoes, peppers, and cabbage) include, but are not limited to, *Lactobacillus plantatum*, *Lactobacillus brevis*, *Leuconostoc mesenteroides*, *Pediococcus cerevisiae*, and mixtures thereof. See Food Biotechnology, 540 (D. Knorr Ed. 1987); C. Pederson, Microbiology of Fermented Foods, 153-209 (2d ed. 1979); U.S. Pat. No. 3,024,116 to Engelland; U.S. Pat. No. 3,403,032 to Etchells et al.; U.S. Pat. No. 3,932,674 to Etchells et al.; U.S. Pat. No. 3,897,307 to Porubcan et al.

Bacteria used in the fermentation of dough formed from cereals (e.g., wheat, rye, rice, oats, barley, and corn) include yeasts such as *Saccharomyces cerevisiae* and *Candida utilis*; and lactic acid bacteria of the genera Lactobacillus, Lactococcus, Pediococcus and Leuconostoc, including, but not limited to *Lactobacillus delbrueckii*, *Lactobacillus leichmanni*, *Lactobacillus plantarum*, *Lactobacillus casei*, *Lactobacillus brevis*, *Lactobacillus fermenti*, *Lactobacillus pastorianus*, *Lactobacillus buchneri*, and *Leuconostoc mesenteroides*. See generally Food Biotechnology, 235-70 (D. Knorr Ed. 1987); U.S. Pat. No. 3,734,743 to Kline and Sugihara; U.S. Pat. No. 3,681,083 to Everson; U.S. Pat. No. 3,993,783 to Khoudokormoff and Langejan; U.S. Pat. No. 3,843,800 to Langejan; U.S. Pat. No. 3,410,692 to Wutzel.

Wine is produced by the fermentation of fruit juice, typically grape juice, with yeasts, such as *Saccharomyces cerevisiae* and *Saccharomyces ellipsoideus*, as well as with a broad variety of lactic acid bacteria including *Pediococcus cerevisiae*, *Lactobacillus plantarum*, *Leuconostoc mesenteroides*, *Leuconostoc dextranicum*, *Leuconostoc cremoris*, *Lactobacillus brevis*, and *Lactobacillus fermenti*. Beer is produced by the fermentation of malt with yeasts such as *Saccharomyces cerevisiae* and *Saccharomyces carlsbergensis*. See C. Pederson, Microbiology of Fermented Foods, 271-309 (2d ed. 1979).

In a particularly preferred embodiment, the present invention is employed for the fermentation of milk with Lactococci (previously classified as the group N Streptococci), such as *Lactococcus lactis*, *Lactococcus cremoris*, and *Lactococcus lactis* biovar. *diacetylactis* (also called *Lactococcus diacetylactis*).

Starter cultures employed in practicing the present invention may be in any physical form, including liquid cultures of the fermentation bacteria in a suitable growth medium, as well as lyophilized cultures and frozen cultures prepared therefrom.

Starter cultures employed in the present invention are preferably defined cultures (i.e., cultures of known bacterial content). Such defined cultures may be either single strain cultures or multiple strain cultures.

D. DISCUSSION

The phage defense rotation strategy disclosed herein incorporates three primary features: (i) each strain carries a defined phage resistance system, (ii) the type or specificity of defense mechanism which is active changes upon each new cycle, and (iii) the same host background is used throughout the rotation sequence. The first feature relies on the use of defined mechanisms of phage resistance as a means of defense. Construction of $Hsp^+$ and $R^+/M^+$ strains assured that each strain contained an inherent, operational mechanism of unique specificity. This contrasts with the use of resistant mutants for which the phage resistance is not stable or well defined, characteristics which often lead to unpredictable behavior in starter rotations.

In the examples below, when the PDRS was inititated with *L. lactis* NCK204 (pTR2030; $Hsp^+$, $R^+/M^+$), fermentative activity was acceptable in the presence of high levels ($10^6$ PFU/ml) of initial phage contamination and low levels of $Hsp^r$ phage ($10^2$ PFU/ml). NCK204 (pTR2030) exhibited phage inhibitory characteristics typical of $Hsp^+$ strains bearing the pTR2030 plasmid. Initiating the sequence with NCK204 ($Hsp^+$, $R^+/M^+$) acted as a cleansing step which effectively reduced the number of phage present in the milk system from an initial level of $10^6$ PFU/ml to a final $10^3$ PFU/ml after the first cycle. Previous reports have indicated that strains containing pTR2030 ($Hsp^+$, $R^+/M^+$) are capable of adsorbing phage and aborting the infection which effectively reduces the number of phage that persist after one cycle of the starter culture activity test. Sing and Klaenhammer, 51 *Appl. Environ. Microbiol.* 1264 (1986). pTR2030 transconjugants ($Hsp^+$) derived from *S. cremoris* strains M43, KH, and HP significantly reduced initial phage titers during starter culture activity tests. Other activity tests using a phage-host system where only Hsp⁺ was operational demonstrated that phage levels were reduced to a similar degree within the first cycle. Therefore, this phenomenon is not limited to the particular strain used in the examples (NCK204) and can be created by introducing pTR2030 or other similar abortive-type phage resistance plasmids into other *lactococcal* strains targeted for use in this type of rotation strategy.

Although reductions in the phage which was sensitive to Hsp⁺ were not solely dependent on pTR2030-encoded R/M activities, the examples indicate that R⁺/M⁺ was essential to NCK204 protection in rotations containing Hsp$^r$ phage. If NCK204 did not carry R⁺/M⁺ and only Hsp⁺ was active, Hsp$^r$ phage would have developed to levels where the activity of R⁺/M⁺ strains following in rotation would be inhibited. Therefore, it is significant that multiple mechanisms (Hsp and R/M) were operational in the first cycle and suggests a preference for at least two different mechanisms within the same strain or the use of isogenic paired strains which carry different mechanisms.

The Examples show that hosts carrying pTR2030 adsorbed phage in the system, however, phage proliferation was severly arrested. This effect is consistent with the specific nature of the pTR2030-encoded abortive infection mechanism and appears to act as a mechanism which essentially "captures phage". Phage adsorption and DNA penetration occurs, however, only a few cells release progeny phage.

The Examples further show that R⁺/M⁺ strains, *L. lactis* NCK347 (pTN20), NCK346 (pTRK11), and NCK344 (pTRK68) also demonstrated characteristics important to the PDRS. When used consecutively in a rotation, the individual R⁺/M⁺ mechanisms encoded by pTN20, pTRK11, and pTRK68 (EOPs of $10^{-3}$ to $10^{-4}$) suppressed phage development where the levels of contamination ($10^2$ PFU/ml) readily inactivated strains which did not contain R/M mechanisms. Higher restriction levels (EOP of $10^{-4}$ to $10^{-5}$) in NCK204 (pTR2030), NCK326 (pTN20, pTRK68), and NCK348 (pTRK11, pTRK68) suppressed development of Hsp$^r$ phage present initially at $10^3$ PFU/ml. The success or failure of any strain or strain combination used in an activity test is contingent on the strength of the phage defense relative to the level and type of phage present intitially. It is significant that the PDRS effectively retarded lytic phages homologous for the *L. lactis* NCK203 hosts and Hsp$^r$ phages, although its effectiveness was based on the level and diversity of phage contamination. Significant levels of modified phage develop after a single cycle of an R/M host in a starter culture activity test that includes a high temperature incubation period. The probability of modified phage appearing has made sole reliance on R/M systems less attractive for construction of phage insensitive strains for commercial application. In the examples, however, plasmid-encoded R/M systems were successfully employed when used as one component in a rotation strategy. Overall, Hsp⁺ strains complemented R⁺/M⁺ strains by reducing initial levels of phage contamination ($10^6$ PFU/ml) to a low level ($10^3$ PFU/ml) where R⁺/M⁺ strains could be effective. In turn, R⁺/M⁺ strains complemented Hsp⁺ strains by inhibiting the development of Hsp$^r$ phages.

The second important feature of the PDRS involves changing the type of phage defense mechanism upon each cycle in the rotation sequence. Although the present use of Hsp⁺ strains in commercial production has been successful, appearance of Hsp$^r$ phage which replicate on pTR2030 hosts will certainly restrict the application and longevity of Hsp⁺ strains. It is suspected that low frequency phage mutation and/or recombination events could generate the Hsp$^r$ phages. R⁺/M⁺ strains used in the PDRS of the Examples were effective at suppressing the development of Hsp$^r$ phages at low levels ($10^2$ to $10^3$ PFU/ml). Therefore, R/M may minimize build-up of Hsp$^r$ phages if they appear. Similarly, the use of two different R/M systems (pTN20, pTRK11) in consecutive sequence will prevent development of modified phage for a single R/M host. Rotation sequences can be designed so that modified phage generated from one R/M host is significantly restricted in the next cycle by a host carrying an R/M system of different specificity. Targeting different steps in the phage lytic cycle with each next rotation will optimize phage inhibition and, therefore, minimize build-up of any mutant or modified phage. This approach should be more effective than the arbitrary employment of strains with undefined defense mechanisms and overall phage sensitivity.

The third important feature of the PDRS is that the same host background (isogenic strains) be used throughout the rotation sequence. Repeated use of the same strain in rotation is ideal because it effectively dilutes out unrelated phage which do not adsorb or replicate on the host being used. This dilution effect works to a certain extent in traditional rotations. However, inadvertant use of phage-related strains and a diversity of hosts appear to perpetuate background phage populations. In the Examples below, isogenic strains carrying different phage resistance mechanisms maintained activity over 9 cycles of the Heap-Lawrence test in the presence of commercial phage composites. This demonstrated the longevity of the PDRS and its ability to maximize the dilution effect. Development of homologous phage for the isogenic strains was minimized by rotation of complementary defenses. Prolonging the use of a single isogenic host reduces the number of strains used in rotation and therefore should improve the consistency of cheesemaking. Limiting the number of host backgrounds employed should also decrease phage diversity in the system.

Lastly, employing a single isogenic host background allows one to monitor for the appearance of new virulent phages in the plant with relative ease. The original host (NCK203 in the examples below), which is deficient in phage defense mechanisms, provides a "super-sensitive" indicator strain. Such a strain increases the overall sensitivity of the phage screening assays and reduces the effort required to monitor for phage relative to traditional rotations where numerous indicator strains (10–30) must be used to screen for the appearance of any new virulent phages.

The present invention is explained in greater detail in the examples which follow. These examples are set forth for illustrative purposes only, and are not to be taken as limiting.

EXAMPLE 1

Bacterial Strains, Plasmids, Bacteriophage and Deposit of Bacterial Strains

The bacterial strains, plasmids, and bacteriophage described herein are listed in Table 1. Lactose fermenting (Lac⁺) *Lactococcus lactis* subsp. *lactis* (*L. lactis*) strains and their bacteriophages were propagated in M17-lactose broth at 30° C. See E. Terzaghi and W. Sandin, *Appl. Microbiol.* 29, 807 (1975). Lac⁻ strains were propagated in M17-glucose broth at 30° C. All stock cultures were stored at –30° C. in the appropriate medium with 10% glycerol. Phages nck203.31 ($\phi$31), nck203.48 ($\phi$48), and nck203.50 ($\phi$50) were propagated and titered on *L. lactis* NCK203. Bacteriophage titers were determined in accordance with known procedures. See E. Terzaghi and W. Sandine, *Appl. Microbiol.* 29, 807 (1975); M. Sanders and T. Klaenhammer. *Appl. Environ. Microbiol.* 47, 979 (1984). Composite HS was composed of 20 individual commercial whey composites and contained approximately 160 independently isolated phages. Phage Composites HR2 or HR3 consisted of Composite HS plus an additional composite containing phages active on *L. lactis* NCK204 (pTR2030; Hsp$^+$ R$^+$/M$^{30}$). These phages were designated Hsp$^r$ and were enumerated on *L. lactis* NCK203 before combination with Composite HS to prepare Composite HS2 and HS3. Hsp$^r$ phages were present in the composites at titers approximating $10^2$ PFU/ml (Composite HR2) and $10^3$ PFU/ml (Composite HR3).

TABLE 1

(a)

| Strain | Relevant Characteristics[a] |
|---|---|
| NCK1 | Hsp$^+$ R/M$^+$ Lac$^+$, MG1363 containing pTR2030, pTR1040, conjugal donor. |
| NCK20 | Lac$^+$ R$^+$/M$^+$, spc-4 rif-5, donor, pTR1041, pTN20 (Higgins et al., 1988) |
| NCK202 | Lac$^-$ Hsp$^-$ R$^+$/M$^+$, str-15, recipient, pTRK68, previously designated *L. lactis* L2FA (Jarvis and Klaenhammer, 1986) |
| NCK203 | Lac$^-$ Hsp$^-$ R$^-$/M$^-$· str-15, recipient, derivative of NCK202, propagating host for φ31 and φ48 (Hill et al., 1989) |
| NCK204 | Lac$^+$ Hsp$^+$, str-15, NCK203 transconjugant, pTR1040, pTR2030 (Jarvis and Klaenhammer, 1986) |
| NCK214 | Per$^+$, str-15, Em$^r$, NCK203 transformant, pTRK104. |
| NCK298 | Lac$^+$ Hsp$^+$ R/M$^+$ Per$^+$, str-15, Em$^r$, NCK214 transconjugant, pTRK104, pTR2030, pTR1040. |
| NCK326 | Lac$^+$ R$^+$/M$^+$, str-15, NCK202 transconjugant, pTN20, pTR1041, pTRK68 (Higgins et al., 1988) |
| NCK336 | Lac$^-$ R$^+$/M$^+$, str-15, Em$^r$, NCK203 transformant, pVS2, pTRK12 |
| NCK337 | Lac$^-$ R$^+$/M$^+$, str-15, Em$^r$, NCK203 transformant, pVS2, pTRK30 |
| NCK338 | Lac$^+$ R$^+$/M$^+$, Em$^r$, NCK344 transformant, pVS2, pTRK12, pTRK68 |
| NCK339 | Lac$^+$ R$^+$/M$^+$, Em$^r$, NCK344 transformant, pVS2, pTRK30, pTRK68 |
| NCK340 | Lac$^+$ R$^+$/M$^+$, spc-4 rif-5, donor, pTRK11 |
| NCK344 | Lac$^+$ R$^+$/M$^+$, pTRK68, previously designated *L. lactis* LMA12 (Sanders et al., 1986) |
| NCK346 | Lac$^+$ R$^+$/M$^+$, str-15, NCK203 transconjugant, pTRK11 |
| NCK347 | Lac$^+$ R$^+$/M$^+$, str-15, NCK203 transconjugant, pTR1041, pTN20 |
| NCK348 | Lac$^+$ R$^+$/M$^+$, str-15, NCK202 transconjugant, pTRK11, pTRK68 |
| T-EK1 | Lac$^+$ Hsp$^+$, donor, pTR1040, pTR2030 (Klaenhammer and Sanozky, 1985) |
| LM2302 | Lac$^-$ R$^-$/M$-$ Hsp$^-$· str-1 ery-2, recipient (Walsh and McKay, 1981) |

(b)

| Bacteriophage | Relevant Characteristics[a] |
|---|---|
| nck203.31 (φ31) | small isometric-headed phage for NCK203 strains (Hill e-t al., 1989) |
| nck203.48 (φ48) | small isometric-headed phage for NCK203 strains, resistant to Hsp$^+$ encoded by pTR2030 (Hsp$^r$) (Hill et al., 1989) |
| nck203.50 (φ50) | small isometric-headed phage for NCK203 strains, resistant to Hsp$^+$ and R/M$^+$ encoded by pTR2030 (Hsp$^r$, R/M$^r$) (Hill et al., 1989) |
| COMPOSITE HS | combination of 20 individual composite whey samples containing approximately 160 independently isolated phage, titer of phage that plaque on NCK203 = $10^6$ PFU/ml (Sanders[b]) |
| COMPOSITE HR2 | composite HS + 4 individual whey samples containing $10^2$ PFU/ml Hsp$^r$ phages (Sanders[b]) |

TABLE 1-continued

| COMPOSITE HR3 | composite HS + 4 individual whey samples containing $10^3$ PFU/ml Hsp$^r$ phages (Sanders[b]) |
|---|---|

(c)

| Plasmid | Relevant Characteristics[a] |
|---|---|
| pTR1040 | Lac$^+$ (Klaenhammer and Sanozky, 1985) |
| pTR1041 | Lac$^+$ (Higgins et al., 1988) |
| pTR2030 | Hsp$^+$ Tra$^+$ (Klaenhammer and Sanozky, 1985) |
| pTRK11 | Lac$^+$ Tra$^+$ R$^+$/M$^+$ (Sing and Klaenhammer, 1989) |
| pTRK12 | R$^+$/M$^+$ (Sing and Klaenhammer, 1989) |
| pTRK30 | R$^+$/M$^+$ (Sing and Klaenhammer, 1989) |
| pTN20 | Tra$^+$ R$^+$/M$^+$ (Higgins et al., 1988) |
| pTRK68 | R$^+$/M$^+$ (Hill et al., 1989) |
| pTRK104 | Per$^+$ |

[a]Lac$^+$, lactose fermenting; Lac$^-$, lactose negative; Hsp$^+$, phage resistance encoded by pTR2030; R$^+$/M$^+$, restriction and modification; Per$^+$, Phage encoded resistance; Tra$^+$, conjugal transfer ability; Sm$^r$, streptomycin resistance; Em$^r$, erythromycin resistance; Sp$^r$, spectinomycin resistance; Rf$^r$, rifamycin resistance; Nis$^r$, nisin resistance; Hsp$^r$, phage resistant to pTR2030.
[b]Miles, Inc., Biotechnology Product Division The following bacterial strains were deposited with the American Type Culture Collection (ATCC), 12301 Parklawn Drive, Rockville, Md. 20852 USA, in accordance with the provisions of the Budapest treaty, on Aug. 10, 1990, and given the Accession numbers indicated parenthetically.

(a) *Lactococcus lactis* subsp. *lactis* NCK348 (ATCC Accession No. 68377);

(b) *Lactococcus lactis* subsp. *lactis* NCK326 (ATCC Accession No. 68378); and (c) *Lactococcus lactis* subsp. *lactis* NCK298 (ATCC Accession No. 68379).

EXAMPLE 2

Conjugation and Phage Resistance

Conjugation was conducted using agar surface matings and Lac$^+$ transconjugants selected on lactose indicator agar as described by McKay et al., *Appln. Environ. Microbiol.* 40, 84 (1980). The following antibiotics were used to select recipients from mating mixes: spectinomycin (spc) 300 ug/ml, rifampicin (rif) 50 ug/ml, streptomycin (str) 1000 ug/ml, and erythromycin (Em) 1.5 ug/ml. The phage resistance and sensitivity of transconjugants was evaluated based on efficiency of plaquing (EOP) and plaque morphology in accordance with known procedures. See T. Klaenhammer. and R. Sanozky, *J. Gen. Microbiol.* 131, 1153 (1985). Plasmid analyses were conducted on transconjugants to confirm the presence of R$^+$/M$^+$ or Hsp$^+$ plasmids as described previously. W. Sing and T. Klaenhammer, *Appl. Environ. Microbiol.* 51, 1264 (1986).

EXAMPLE 3

Protoplast Transformation

Protoplast transformation was conducted using the procedure described by Kondo and McKay with modifications by Hill et al. See C. Hill et al., *Appl. Environ. Microbiol.* 55, 1684 (1989); J. Kondo and L. McKay, *Appl. Environ. Microbiol.* 48, 252 (1984); J. Kondo and L. McKay, *Appl. Environ. Microbiol.* 43, 1213 (1982). Vector pVS2 (Em$^r$ Cm$^r$) (49) was used for cotransformation in a vector:plasmid DNA (w/w) ratio of 1:50. Em$^r$ transformants were screened for phage resistance (R/M) by cross-streaking against phage p2 on M17G agar plates. Dilutions of phage p2 ($10^1$–$10^6$ PFU/ml) were swabbed onto M17G agar plates in one direction. Broth culture of each transformant was then streaked in the opposite direction from lowest to highest phage concentration. Phage resistance was scored based on comparative growth on areas where phage concentration was higher. Plasmid analyses were conducted on all transformants to confirm DNA acquisition.

EXAMPLE 4

Starter Culture Activity Tests

The Heap-Lawrence starter culture activity test, H. Heap and R. Lawrence, *N.Z.J. Dairy Sci. Technol.* 11, 16 (1976); H. Heap and R. Lawrence, *N.Z.J. Dairy Sci. Technol.* 15, 91 (1981), was conducted using a time/temperature incubation profile of 100 min at 30° C., 190 min 40° C., and 100 min 30° C. Test tubes containing 10 ml of 11% reconstituted skim milk (RSM) supplemented with 1% glucose and 0.25% casamino acids were steamed for 1 h, cooled to 30° C., and inoculated with 0.2 ml of culture. Each culture was propagated 16 h at 22° C. in milk prior to inoculation of milk tubes for the activity test. In some experiments, 200 ul of phage preparation was inoculated into the culture (10 ml 11% RSM) initially and, thereafter, 200 ul of whey from the previous cycle was added at the beginning of subsequent cycles. This procedure was designated "whey only supplement". In other experiments, 200 ul of phage preparation was inoculated into the culture (10 ml 11% RSM) initially and fresh phage was used to supplement whey after each rotation. Following the first cycle, 100 ul of whey from the previous cycle +100 ul of the original phage preparation were added at the beginning of each next cycle. This phage supplement was designated "phage+whey". Starter activity was evaluated based on final pH. Rotation sequences were terminated when strains failed to lower the milk pH below 6.0 and high levels of phage were detected ($10^8$–$10^9$ PFU/ml).

EXAMPLE 5

Determination of Whey Bacteriophage Titer

Whey samples were prepared by addition of 0.5 ml of 10% lactic acid to coagulate cultures after completion of the starter culture activity test. The coagulated cultures were vortexed and a 1.5 ml sample dispensed into a microfuge tube. Whey was obtained after centrifugation for 5 min. Whey dilutions (10 ul of $10^{-1}$ to $10^{-8}$) were spotted on sensitive indicator lawns prepared using the agar overlay technique described previously. See E. Tezaghi and W. Sandine, *Appl. Microbiol.* 29, 807 (1975). Initial phage titers for each cycle were determined using the above procedure for milk with added phage or whey only. Bacteriophage titers were estimated based on the number of plaques formed per 10 ul of whey preparation and reported to the nearest order of magnitude. The lowest detectable limit was $10^2$ PFU/ml.

EXAMPLE 6

Starter Rotation Sequences

The strain rotation sequences tested and order of strains used are represented in Table 2. Phages φ31, φ48 or phage composites HS, HR2, and HR3 were used accordingly with each sequence. Control experiments included: (i) strains deficient in R/M or Hsp (no protection), (ii) phage or whey only (initial titer), and (iii) culture only (starter activity).

TABLE 2

Sequence of R/M and Hsp Derivatives of *L. lactis* NCK203 Used in Culture Rotations

| | CYCLE NUMBER | | |
|---|---|---|---|
| Sequence | 1, 4, 7 | 2, 5, 8 | 3, 6, 9 |
| Sequence A: | | | |
| System[a] | R/M I | R/M II | R/M III |
| Strain[b] | NCK347 | NCK346 | NCK344 |
| Resistance Level[c] | $10^{-4}$ | $10^{-3}$ | $10^{-3}$ |
| Sequence B: | | | |
| System | R/M I | R/M II | HSP I |
| Strain[b] | NCK347 | NCK346 | NCK204 |
| Resistance | $10^{-4}$ | $10^{-3}$ | $<10^{-9}$ |
| Sequence C: | | | |
| System | HSP I | R/M I | R/M II |
| Strain[b] | NCK204 | NCK347 | NCK346 |
| Resistance Level | $<10^{-9}$ | $10^{-4}$ | $10^{-3}$ |
| Sequence D: | | | |
| System | HSP I | R/M IV | R/M V |
| Strain[b] | NCK204 | NCK326 | NCK348 |
| Resistance Level | $<10^{-9}$ | $10^{-5}$ | $10^{-5}$ |

[a]R/M I (pTN20), R/M II (pTRK11), R/M III (pTRK68), R/M IV (pTN20, pTRK68), R/M V (pTRK11, pTRK68).
[b]All strains are derivatives of *L. lactis* NCK203
[c]EOP for small isometric phage φ31

EXAMPLE 7

Construction of Phage-Resistant Strains

Strains harboring various plasmid-encoded phage defense systems were constructed for use in starter rotation sequences using conjugation or transformation (Table 3). Donor strains carrying the self-transmissible plasmids pTR2030 (Tra$^+$, Hsp$^+$) pTRK11 (Tra$^+$, R$^+$/M$^+$), or pTN20 (Tra$^+$, R$^+$/M$^+$) were used in conjugation experiments. Cotransformation of plasmids pTRK12 (R$^+$/M$^+$) or pTRK30 (R$^+$/M$^+$) with vector pVS2 (Em$^r$) was detected by selection of Em$^r$ transformants and cross-streaking against phage to determine (R/M). R/M and Hsp systems were transferred successfully into the phage-sensitive recipient, *L. lactis* NCK203 or its R$^+$/M$^+$ parental strains NCK202 (pTRK68, Lac$^-$ R$^+$/M$^+$) and NCK344 (pTRK68, Lac$^+$ R$^+$/M$^+$) (Table 3). Phage φ31 did not plaque on the Hsp$^+$ transconjugant *L. lactis* NCK204 (pTR2030) (EOP<$10^{-9}$). The EOP of φ31 on *L. lactis* NCK203 R$^+$/M$^+$ transconjugants and transformants ranged from $10^{-3}$ to $10^{-4}$. Multiple levels of restriction (EOP of $10^{-5}$) were demonstrated by R$^+$/M$^+$ transconjugants of NCK202 (pTRK68) or transformants of NCK344 (pTRK68) due to the effect of combining pTRK68 (R$^+$/M$^+$) with pTRK11 (R$^+$/M$^+$), pTRK12 (R$^+$/M$^+$), or pTN20 (R$^+$/M$^+$). In contrast, *L. lactis* NCK344 transformants containing pTRK30 (R$^+$/M$^+$) with pTRK68 (R$^+$/M$^+$) failed to demonstrate multiplicative levels of restriction. *L. lactis* NCK344 (pTRK68, R$^+$/M$^+$) encoded a R/M system with specificity distinct from NCK346 (pTRK11, R$^+$/M$^+$), NCK337 (pTRK30, R$^+$/M$^+$) or NCK347 (pTN20, R$^+$/M$^+$).

TABLE 3

Transfer of phage resistance plasmids into isogenic recipients
L. lactis NCK202, NCK203, NCK344 and efficiency of plaquing of
phage φ31 on phage resistant constructs

| Donor[a] | Plasmid[b] | Recipient | Phage Resistant Recombinants | Relevant Plasmids[c] | EOP[d] | Phage Resistance System |
|---|---|---|---|---|---|---|
|  | pTRK12 | NCK203 | NCK336 | pTRK12 (R⁺/M⁺) | $1.9 \times 10^{-2}$ |  |
|  | pTRK30 | NCK203 | NCK337 | pTRK30 (R⁺/M⁺) | $3.4 \times 10^{-3}$ |  |
|  |  |  | NCK344 | pTRK68 (R⁺/M⁺) | $4.2 \times 10^{-3}$ | R/M III |
| T-EK1 |  | NCK203 | NCK204 | pTR2030 (Hsp⁺) | $<10^{-9}$ | HSP I |
| NCK340 |  | NCK203 | NCK346 | pTRK11 (R⁺/M⁺) | $5.7 \times 10^{3}$ | R/M II |
| NCK20 |  | NCK203 | NCK347 | pTN20 (R⁺/M⁺) | $2.4 \times 10^{-4}$ | R/M I |
|  | pTRK12 | NCK344 | NCK338 | pTRK12 (R⁺/M⁺) pTRK68 (R⁺/M⁺) | $1.3 \times 10^{-5}$ |  |
|  | pTRK30 | NCK344 | NCK339 | pTRK30 (R⁺/M⁺) pTRK68 (R⁺/M⁺) | $2.0 \times 10^{-3}$ |  |
| NCK340 |  | NCK202 | NCK348 | pTRK11 (R⁺/M⁺) pTRK68 (R⁺/M⁺) | $8.6 \times 10^{-5}$ | R/M V |
| NCK20 |  | NCK202 | NCK326 | pTN20 (R⁺/M⁺) pTRK68 (R⁺/M⁺) | $3.9 \times 10^{-5}$ | R/M IV |

[a]Donor used in conjugation;
[b]Plasmid used in cotransformation;
[c]plasmids harbored by recombinants;
[d]EOP of φ31

EXAMPLE 8

Effect of Alternating R/M Systems on Phage Development and Starter Activity

R⁺/M⁺ strains *L. lactis* NCK347 (pTN20), NCK346 (pTRK11), and NCK344 (pTRK68) were used in Sequence A (R/M I, R/M II, R/M III) to determine whether alternating R/M mechanisms inhibited phage development during starter culture activity tests. The order of strains used in Sequence A was established to maximize the degree of restriction that the phage would encounter from each cycle to the next R⁺/M⁺ host. Since φ31 demonstrated an EOP of $2.4 \times 10^{-4}$ on *L. lactis* NCK347 (pTN20), while NCK346 (pTRK11) and NCK344 (pTRK68) restricted at lower levels of $5.7 \times 10^{-3}$ and $4.2 \times 10^{-3}$, respectively, NCK347 was chosen to initiate the rotation sequence. Phage φ31 propagated on *L. lactis* NCK347 (pTN20) (φ31.NCK347) plaqued on *L. lactis* NCK346 (pTRK11) at a lower EOP ($9.2 \times 10^{-5}$) than on *L. lactis* NCK344 (pTRK68) ($5.8 \times 10^{-2}$); therefore, NCK346 was used after NCK347 in rotation. The Sequence A rotation was initiated with either $10^3$ PFU/ml or $10^2$ PFU/ml input phage φ31. Whey only was supplemented to each subsequent cycle. When $10^3$ PFU/ml φ31 were added initially, significant levels of phage developed ($10^7$ PFU/ml) within the first cycle. Sequence A failed after the second cycle and, culture activity was inhibited (pH 6.0). When $10^2$ PFU/ml φ31 were added initially, some phage development was evident upon the first two cycles. However, phage levels were reduced by the third cycle and culture activity (pH 5.3 to 5.4) was maintained throughout 9 cycles. Starter cultures used in Sequence A without phage added produced acceptable levels of activity (pH 5.0–5.3), whereas *L. lactis* NCK203, the propagating host for φ31, failed in the first cycle when challenged with $10^2$ PFU/ml of φ31 (data not shown). Each R⁺/M⁺ strain (NCK347, NCK346, or NCK344) used individually in repeated cycles failed within the second or third cycle due to development of modified φ31 phages ($10^8$–$10^9$ PFU/ml). These data indicated that use of R/M systems encoded by pTN20, pTRK11, and pTRK68 were effective at protecting *L. lactis* NCK203 in rotation when the initial levels of contamination did not exceed $10^2$ PFU/ml.

EXAMPLE 9

Reduction in Phage Levels by Rotation of an Hsp⁺ Strain

Figure 1B:
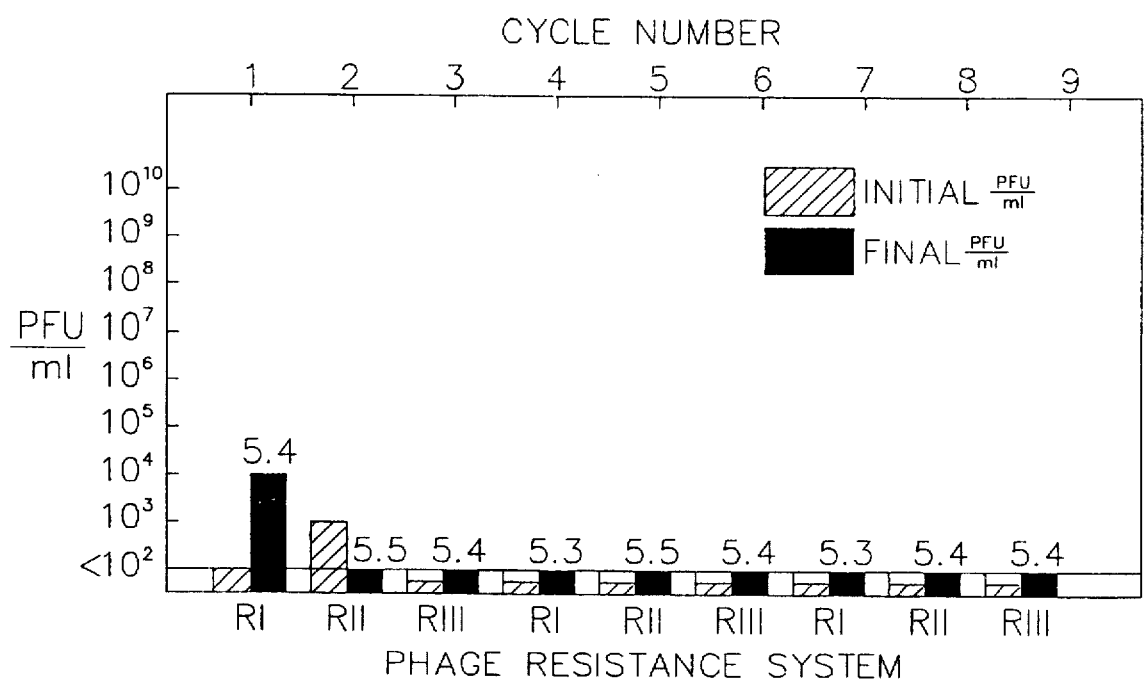

*L. lactis* NCK204 (pTR2030; Hsp⁺, R⁺/M⁺) was substituted for a R⁺/M⁺ strain in the Sequence B rotation (R/M I, R/M II, HSP) (Table 2). This sequence was initiated with $10^6$ PFU/ml φ31 followed by whey only supplement in subsequent cycles. Minimal culture activity within the first two cycles using R⁺/M⁺ strains NCK347 (pTN20) and NCK346 (pTRK11) (FIG. 1), indicated that phage development was not significantly inhibited. Phage reached high levels ($10^8$ PFU/ml) within the first two cycles. When NCK204 (pTR2030; Hsp⁺, R⁺/M⁺) was used in the third cycle, the level of phage was reduced from $10^6$ to $10^3$ PFU/ml. Thereafter, rotation of R⁺/M⁺ and Hsp⁺ strains proceeded up to 9 cycles without loss of culture activity.

Figure 2:
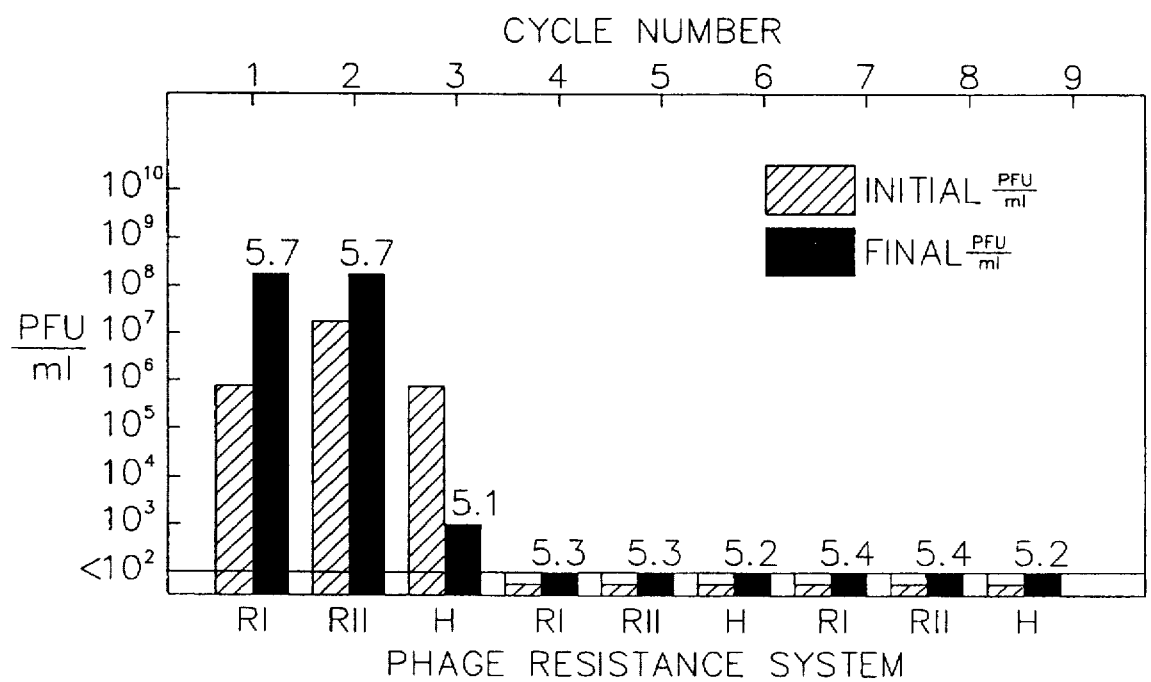
FIG. 2 shows, for Rotation Sequences C and D, the effect of initiating the rotation sequence with Hsp$^+$ strain *L. lactis* NCK204 on phage development during starter culture activity tests. Initial $\phi$31 titer=10$^6$ PFU/ml; whey only added after the first cycle. H=NCK204 (pTR2030), RI=NCK347 (pTN20), RII=NCK346 (pTRK11). Final pH is indicated on top of the bar representing final PFU/ml.

Since *L. lactis* NCK204 (pTR2030; Hsp⁺, R⁺/M⁺) reduced high initial phage levels to low levels, NCK204 was used to initiate rotation Sequence C (HSP, R/M I, R/M II) where $10^6$ PFU/ml φ31 was added initially followed by whey only supplemented upon each new cycle. FIG. 2 shows that phage φ31 populations were reduced from $10^6$ to $10^3$ PFU/ml after the first cycle. Starter culture activity was maintained at (pH 4.9–5.4) throughout all rotations and phage levels held at $<10^2$ PFU/ml after 3 cycles of R⁺/M⁺ strains. Regardless of whether the R⁺/M⁺ strains restricted φ31 at EOPs of $10^{-3}$ to $10^{-4}$ (R/M I and R/M II) (FIG. 2) or $10^{-5}$ (Sequence D, R/M IV and R/M V) (data not shown), the rotation sequences maintained adequate activity throughout 9 cycles. When the R⁺/M⁺ strains used after the Hsp cycle were replaced by the φ31 propagating host *L. lactis* NCK203, culture failure occurred within three cycles as a result of high phage levels ($10^8$ PFU/ml) (data not shown).

EXAMPLE 10

Figure 3A:
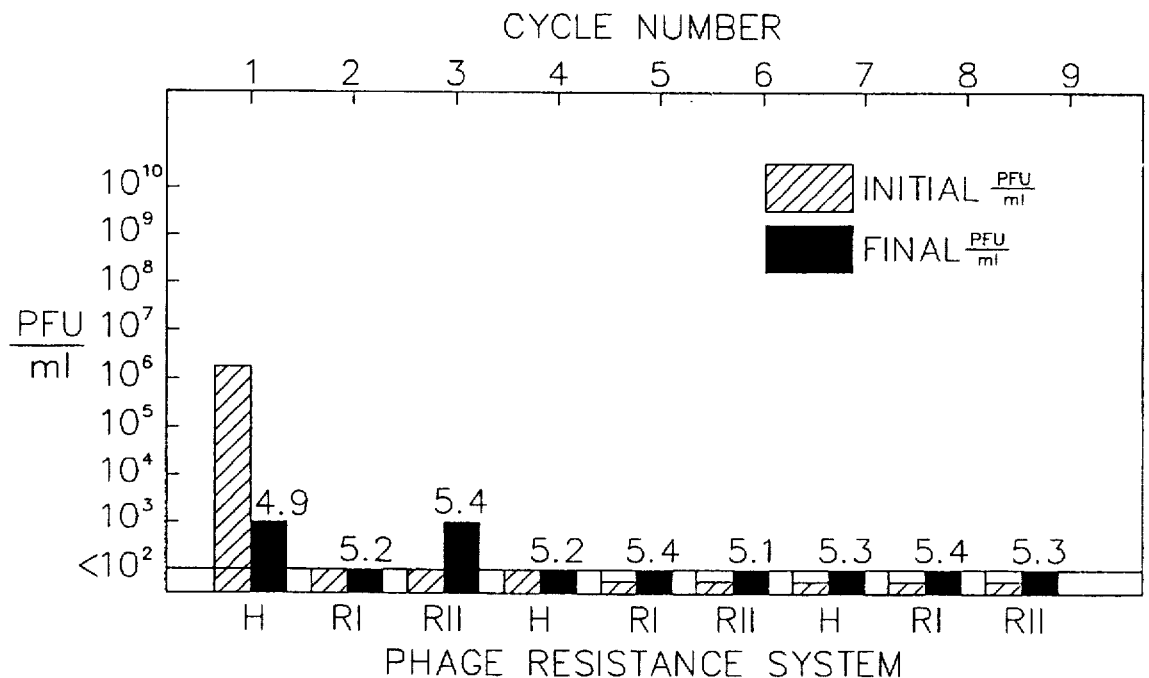
FIGS. 3A and 3B show the effect of $\phi$48 (Hsp$^r$) on rotation Sequences C & D during starter culture activity tests. H=NCK204 (pTR2030), RIV=NCK326 (pTN20, pTRK68), RV=NCK348 (pTRK11, pTRK68). Final pH is indicated on top of the bar representing final PFU/ml.
Figure 3B:
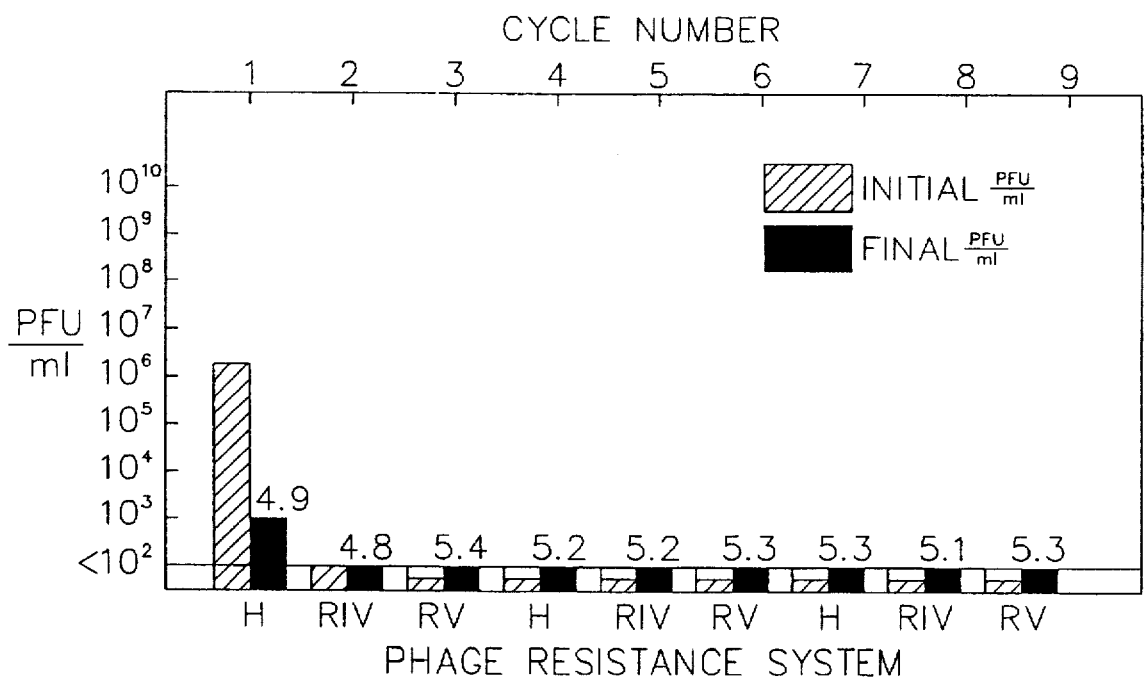

Inhibition of an Hsp Resistant Phage by Rotation of Hsp$^+$ and R$^+$/M$^+$ Strains Rotation Sequence D (Hsp, R/M IV, R/M V) was challenged with phage φ48 which is resistant to the Hsp resistance mechanism encoded by pTR2030 (Hsp$^r$). Although Hsp$^+$ encoded by pTR2030 in NCK204 is not effective against φ48, the pTR2030-encoded R/M system restricts φ48 at an EOP of $10^{-3}$. The other two strains in the seqeuence, L. lactis NCK326 (pTN20, R$^+$/M$^+$; pTRK68, R$^+$/M$^+$) and NCK348 (pTRK11, R$^+$/M$^+$; pTRK68, R$^+$/M$^+$), restricted φ48 at EOPs of $10^{-5}$. Sequence D (Table 2) was inititated with $10^2$ and $10^4$ PFU/ml φ48 with whey only supplement added in subsequent cycles. Initial levels of $10^2$ PFU/ml φ48 did not disrupt the starter culture activity of Sequence D over 9 cycles (FIG. 3A). Operation of R/M encoded by pTR2030 in cycle 1 was essential to maintaining activity and significantly limited development of φ48 to a degree where the following R$^+$/M$^+$ strains could control phage development. Phage φ48 was held to levels less than $10^2$ PFU/ml after the first two rotations. In contrast, initial φ48 levels of $10^4$ PFU/ml significantly inhibited Sequence D starter activity (FIG. 3B). Phage φ48 developed to high levels ($10^8$ PFU/ml) after the first rotation and caused total culture failure within the fourth cycle (FIG. 3B). Repeated cycles with L. lactis NCK204 (Hsp$^+$) or L. lactis NCK203 (φ48 propagating host) after an initial NCK204 (Hsp$^+$) cycle resulted in culture failure within 3 cycles (data not shown) when initial φ48 levels were $10^2$ or $10^4$ PFU/ml. Therefore, rotations using Hsp and R/M mechanisms to protect a single host represented an improvement over use of Hsp alone in rotations where Hsp$^r$ phage were present.

EXAMPLE 11

Starter Culture Activity in the Presence of Industrially Significant Phages

The Sequence D rotation (HSP, R/M III, R/M IV) was evaluated for fermentative activity and longevity in the presence of phage isolated from the cheesemaking environment (Table 4). Phage composites (Composite HS, HR2, HR3; Table 1), prepared from commercial whey samples, were inoculated into the first cycle. In each subsequent cycle, whey from the previous cycle was supplemented (+) or not supplemented (−) with the original phage composite before addition. Composite HS contained approximately 160 independently isolated phages in addition to $10^6$ PFU/ml of phage specific for the L. lactis NCK203 host background. Composites HR2 and HR3 contained all Composite HS phages plus low ($10^2$ PFU/ml) or higher levels ($10^3$ PFU/ml) of Hsp$^r$ phages, respectively. When Sequence D was challenged with Composite HS (+), activity was maintained (pH 5.0 to 5.4) over 9 cycles. If the NCK204 (Hsp$^+$ R$^+$/M$^+$) cycle was followed by a phage susceptible host (L. lactis NCK203), failure occurred after 2 cycles. Sequence D performed adequately in the presence of approximately $10^6$ PFU/ml of commercially significant phage added via a combination of whey and Composite HS prior to each cycle.

The rotation sequence was also challenged with Composite HR2 (Table 4). Again, activity was maintained (pH 5.2 to 5.6) over 9 cycles when whey from each cycle was supplemented (+) with Composite HR2. Rotation Sequence D maintained activity when the phage composite HR3 was not added (−) after each rotation, but lost activity when Composite HR3 was added after each rotation (+) (Table 4). When NCK204 (pTR2030) was followed by a phage sensitive host (NCK203) or NCK204 (pTR2030) was used repeatedly, starter failure occurred within the second cycle. Therefore, Sequence D provided acceptable activity in the presence of a high titer (>$10^6$ PFU/ml) phage composite including approximately 160 independently isolated phages from commercial whey, some of which ($10^6$ PFU/ml) can attack this host background and others ($10^2$ PFU/ml) which can attack Hsp$^+$ strains. Sequence D did not perform beyond 3 cycles when whey was supplemented with $10^3$ PFU/ml of fresh Hsp$^r$ phage at the beginning of each cycle.

TABLE 4

Starter culture activity of strains used in rotation Sequence C against whey composites with and without Hsp resistant phage

| PHAGE COMPOSITE[a] (+/−)[b] | SEQUENCE[c] | FINAL pH CYCLE NUMBER | | | | | | | | |
|---|---|---|---|---|---|---|---|---|---|---|
| | | 1 | 2 | 3 | 4 | 5 | 6 | 7 | 8 | 9 |
| HS (+) | [H, RMIV, RMV] | 5.0 | 5.0 | 5.4 | 5.0 | 5.2 | 5.5 | 5.0 | 5.2 | 5.3 |
| HS (+) | [H, S, S] | 5.0 | 6.2[d] | | | | | | | |
| HR2 (+) | [H, RMIV, RMV] | 5.5 | 5.5 | 5.4 | 5.2 | 5.2 | 5.6 | 5.2 | 5.4 | 5.4 |
| HR2 (+) | [H, S, S] | 5.5 | 6.3[d] | | | | | | | |
| HR2 (+) | [H, H, H] | 5.5 | 6.4[d] | | | | | | | |
| HR3 (−) | [H, RMIV, RMV] | 5.7 | 5.5 | 5.4 | 5.0 | 5.2 | 5.0 | 5.0 | 5.2 | 5.3 |
| HR3 (+) | [H, RMIV, RMV] | 5.7 | 5.5 | 6.4[d] | | | | | | |
| HR3 (−) | [H, S, S] | 5.7 | 6.3[d] | | | | | | | |
| HR3 (−) | [H, H, H] | 5.7 | 6.3[d] | | | | | | | |

[a]HS = Composite HS (contains approximately 160 independently isolated phage, titer of phage that plaque on sensitive host NCK203 = $10^6$ PFU/ml; HR2 = Composite HR2 (Composite HS including $10^2$ PFU Hsp$^r$ phage/ml); HR3 = Composite HR3 (Composite HS including $10^3$ PFU Hsp$^r$ phage/ml)
[b](+) whey + phage composite added to start next rotatio; (−) whey only added to start next rotation TABLE 4-continued Starter culture activity of strains used in rotation Sequence C
against whey composites with and without Hsp resistant phage

| PHAGE COMPOSITE[a] | | FINAL pH CYCLE NUMBER | | | | | | | | |
|---|---|---|---|---|---|---|---|---|---|---|
| (+/−)[b] | SEQUENCE[c] | 1 | 2 | 3 | 4 | 5 | 6 | 7 | 8 | 9 |

[c][H, RMIV, RMV] = Sequence D (Table 2); [H, S, S] = Hsp, sensitive, sensitive; S = NCK203, phage sensitive host; [H, H, H] = Hsp, Hsp, Hsp; H = NCK204.
[d]starter failure (final pH 6.0–6.5)

EXAMPLE 12

Construction of Complementary Phage Defense Systems in PDRS Strains

L. lactis NCK298 (pTR2030, pTRK104) was constructed in order to combine complementary phage defenses in a single strain and provide greater resistance to Hsp[r] phages. To construct pTRK104, the Hsp[r] phage nck202.50 (phage 50, 29.8 kb) was digested with BamH1 and HinIII and shotgun cloned into similarly digested pBluescript. A 4.5 kb cloned insert was subcloned into the streptococcal—Escherichia coli shuttle vector, pSA3, (Dao and Ferretti, 49 Appl. Environ. Microbiol 115 (1985)), to create pTRK103. Plasmid pTRK103 was digested with EcoRV, religated and transformed to E. coli DH1. One recombinant plasmid, designated pTRK104, contained a 1.4 kb EcoRV-HindIII insert.

pTRK104 was isolated and transformed via protoplast transformation (Hill et al., 55 Appl. Environ, Microbiol. 1684 (1989)) into L. lactis NCK203 to form NCK214. In this host background, pTRK104 directs a resistance phenotype designated Per ("phage encoded resistance") against Hsp[r] phage 50. The Per[+] phenotype is defined as pinpoint plaque formation by phage 50 at a reduced EOP (ca. 0.35) on NCK214. The per region appears to contain a phage origin of replication which, in trans, interferes with phage replication. Whereas Per[+] restricts the plaque size and plaquing efficiency of the Hsp[r] phage 50, it is ineffective against phage 31.

In order to combine pTR2030 and pTRK104 into a single host, pTR2030 was introduced to NCK214 (containing pTRK104) by solid surface conjugation with the donor strain NCK1 [containing pTR2030 (Hsp[+] R/M[+]) and pTR1040 (Lac[+])]. Lac[+] (pTR1040) Em[r] (pTRK104) transconjugants were screened for the presence of pTR2030. One transconjugant, NCK298, containing both pTR2030 and pTRK104 was selected and examined for combined resistance to phages 50 and 31. NCK298 is completely resistant to phage 31 in standard plaque assays, a typical reaction for this phage on pTR2030-bearing hosts. NCK298 also displays the typical Per[+] response against phage 50. Growth of NCK298 in broth culture was not retarded when both phage 50 and 31 were present at initial levels of 10[6] pfu/ml. The phage resistance mechanisms on pTR2030 and pTRK104 are complementary and operate simultaneously in the L. lactis NCK203 background to prevent infection by either Hsp[r] and Hsp[s] phages which are virulent for this host strain. Such strains containing complementary defense systems can be incorporated into the PDRS in order to minimize the appearance of new phages and retard the proliferation of existing virulent phages.

EXAMPLE 13

Preparation of Multiple Strain Starter Cultures for Use in PDRS Strategies

Each rotation cycle can also be conducted with paired or multiple strain starters, composed of two or more isogeneic strains, bearing different phage defense systems. For example, a multiple strain combination such as [NCK326+NCK298+NCK348] can be used repeatedly in each cycle or rotated using alternative formulations of another multiple strain or a paired composite such as [NCK336+NCK337]. In these cases, even non-isogeneic strains, also constructed with the appropriate phage defense systems, could be substituted in selected cycles of the PDRS.

Strain composites of NCK326 (pTN20, pTRK68), NCK298 (pTR2030, pTRK104), and NCK348 (pTRK11, pTRK68) are prepared via standard procedures. See, e.g., R. Lawrence et al., 43 J. Dairy Res. 141 (1976); Porubcan and Sellars, Chapter 3, Lactic Starter Culture Concentrates, (in) Microbial Technology, 2nd edition, Peppler and Perlman (ed) Volume 1, pp. 59–92 (1979); Prentice and Neves, The Role of Microorganisms in the Dairy Industry, J. Appl. Bacteriol. Symposium Supplement, 43S-57S (1986), using mother cultures, bulk cultures, or direct-to-vat frozen or lyophilized culture concentrates. The preferred methods are the following:

In order to minimize strain imbalance the number of generations should be minimized in the preparation of the multiple strain starter culture. If possible, separate bulk cultures for each strain are prepared and mixed in equal volumes immediately prior to inoculation of the fermentation vat. Individual frozen or lyophilized culture concentrates are then prepared from the mother culture. Multiple strain composites result when the fermentation vat is inoculated with two or more concentrated cultures of single strains that can be used in direct-to-vat applications.

Prepare cell concentrates of each culture, mix in equal volume, and freeze or lyophilize the mixture in an appropriate suspension medium. The frozen or dried concentrate can then be inoculated directly into bulk cultures or fermentation vats.

For example, NCK326, NCK298, and NCK348 were propagated separately in M17-glucose broth to cell concentrations approximating 10[9] CFU/ml; 5 ug/ml erythromycin was supplemented to M17-glucose broth cultures of NCK298 to maintain selection for pTRK104 (Em[r], Pe[r]). The cells were centrifuged and resuspended in 1/10th volume of fresh 11% non-fat dry milk, pH 6.5. Following resuspension, each was mixed in equal volumes by aliquoting into common tubes for freezing. The 1:1:1 mixture was frozen and stored at −70C. For use in starter culture activity tests, one frozen sample was thawed at room temperature and immediately inoculated at the appropriate levels into the 11%

NFDM supplemented with 0.5% glucose, 0.5% yeast extract, and 0.5% caseoamino acids, pH 6.5. The multiple strain starter culture achieved a final pH of 4.8–5.0 after incubation over the time-temperature conditions of the starter culture activity test.

The foregoing examples are illustrative of the present invention, and are not to be construed as limiting thereof. The invention is defined by the following claims, with equivalents of the claims to be included therein.

That which is claimed is:

1. A phage defense rotation strategy for use in the successive fermentations of a substrate in a fermentation plant, comprising:

(a) fermenting said substrate with a first bacterial culture comprising a bacterial strain capable of fermenting the substrate and carrying a first DNA-encoded phage defense mechanism; and then (b) fermenting said substrate with a second bacterial culture comprising a second bacterial strain isogenic with said first bacterial strain and having the same bacteriophage binding characteristics as said first bacterial strain, wherein the second strain carries a second DNA-encoded phage defense mechanism different from the first phage defense mechanism.

2. A method according to claim 1, wherein step (b) is followed by repeating step (a).

3. A method according to claim 1, wherein said fermenting steps are cyclically repeated.

4. A method according to claim 1, wherein step (b) is followed by the step of:

(c) fermenting said substrate with a third bacterial culture comprising a bacterial strain isogenic with said first and second strains and having the same bacteriophage binding characteristics as said first and second bacterial strains, wherein the third strain carries a DNA-encoded phage defense mechanism different from the first and second phage defense mechanisms.

5. A method according to claim 4, wherein step (c) is followed by repeating step (a) or step (b).

6. A method according to claim 4, wherein said fermenting steps are cyclically repeated.

7. A method according to claim 1, wherein said substrate is nonsterile.

8. A method according to claim 1, wherein said first and second bacterial cultures comprise pure cultures.

9. A method according to claim 1, wherein said first and second bacterial cultures comprise mixed bacterial cultures.

10. A method according to claim 1, wherein said substrate is a human food substrate.

11. A method according to claim 1, wherein said substrate is milk.

12. A method according to claim 1, wherein said first and second bacterial strains comprise *lactococci*.

13. A method according to claim 1, wherein said first and second phage defense mechanisms are carried by plasmids.

14. A method according to claim 1, wherein said first and second phage defense mechanisms are selected from the group consisting of prevention of adsorption (Ads), restriction and modification (R/M), abortive infection (Hsp), and phage encoded resistance (Per).

15. A method according to claim 1, wherein said first phage defense mechanism is carried by a plasmid selected from the group consisting of (a) the plasmid pTR2030, which encodes phage resistance phenotype and conjugal transfer phenotype upon expression in *lactococci*, and (b) a derivative of pTR2030, the derivative encoding the phage resistance phenotype encoded by the plasmid pTR2030 upon expression in *lactococci*.

16. A bacterial culture capable of fermenting a substrate, comprising:

(a) a first bacterial strain carrying a first DNA-encoded phage defense mechanism; and (b) a second bacterial strain isogenic with said first strain and having the same bacteria phage binding characteristics as said first bacterial strain, wherein said second strain carries a DNA-encoded phage defense mechanism different from said phage defense mechanism carried by said first strain.

17. A culture according to claim 16, further comprising a third bacterial strain isogenic with said first and second strains and having the same bacteriophage binding characteristics as said first and second bacterial strains, wherein said third strain carries a DNA-encoded phage defense mechanism different from said phage defense mechanisms carried by said first and second strains.

18. A culture according to claim 16, wherein said culture is a pure culture free of non-isogenic strains.

19. A culture according to claim 16, wherein said culture is a mixed culture containing non-isogenic strains.

20. A culture according to claim 16, wherein said culture is capable of fermenting a human food substrate.

21. A culture according to claim 16, wherein said culture is capable of fermenting milk.

22. A culture according to claim 16, wherein said first and second bacterial strains comprise *lactococci*.

23. A culture according to claim 16, wherein said first and second phage defense mechanisms are carried by plasmids.

24. A culture according to claim 16, wherein said first and second phage defense mechanisms are selected from the group consisting of prevention of adsorption (Ads), restriction and modification (R/M), abortive infection (Hsp), and phage encoded resistance (Per).

25. A culture according to claim 16, wherein said first phage defense mechanism is carried by a plasmid selected from the group consisting of (a) the plasmid pTR2030, which encodes phage resistance phenotype and conjugal transfer phenotype upon expression in *lactococci*, and (b) a derivative of pTR2030, the derivative encoding the phage resistance phenotype encoded by the plasmid pTR2030 upon expression in *lactococci*.

26. A phage defense rotation strategy for use in the successive fermentations of a milk substrate in a fermentation plant, comprising:

(a) fermenting said substrate with a *lactococcal* bacterial culture comprising a bacterial strain capable of fermenting the substrate and carrying a first DNA-encoded phage defense mechanism; and then (b) fermenting said substrate with a second *lactococcal* bacterial culture comprising a second bacterial strain isogenic with said first bacterial strain and having the same bacteriophage binding characteristics as said first bacterial strain, wherein the second strain carries a second DNA-encoded phage defense mechanism different from the first phage defense mechanism.

27. A method according to claim 26, wherein step (b) is followed by repeating step (a).

28. A method according to claim 26, wherein said fermenting steps are cyclically repeated.

29. A method according to claim 26, wherein step (b) is followed by the step of:

(c) fermenting said substrate with a third *lactococcal* bacterial culture comprising a bacterial strain isogenic with said first and second strains and having the same bacteriophage binding characteristics as said first and second bacterial strains, wherein the third strain carries a DNA-encoded phage defense mechanism different from the first and second phage defense mechanisms.

30. A method according to claim 29, wherein step (c) is followed by repeating step (a) or step (b).

31. A method according to claim 29, wherein said fermenting steps are cyclically repeated.

32. A method according to claim 26, wherein said substrate is nonsterile.

33. A method according to claim 26, wherein said first and second bacterial cultures comprise pure cultures.

34. A method according to claim 26, wherein said first and second bacterial cultures comprise mixed bacterial cultures.

35. A method according to claim 26, wherein said first and second phage defense mechanisms are carried by plasmids.

36. A method according to claim 26, wherein said first and second phage defense mechanisms are selected from the group consisting of prevention of adsorption (Ads), restriction and modification (R/M), abortive infection (Hsp), and phage encoded resistance (Per).

37. A method according to claim 26, wherein said first phage defense mechanism is carried by a plasmid selected from the group consisting of (a) the plasmid pTR2030, which encodes phage resistance phenotype and conjugal transfer phenotype upon expression in *lactococci*, and (b) a derivative of pTR2030, the derivative encoding the phage resistance phenotype encoded by the plasmid pTR2030 upon expression in *lactococci*.

38. A bacterial culture capable of fermenting a milk substrate, comprising:

(a) a first *lactococcal* bacterial strain carrying a first DNA-encoded phage defense mechanism; and (b) a second *lactococcal* bacterial strain isogenic with said first strain and having the same bacteriophage binding characteristics as said first bacterial strain, wherein said second strain carries a DNA-encoded phage defense mechanism different from said phage defense mechanism carried by said first strain.

39. A culture according to claim 38, further comprising a third *lactococcal* bacterial strain isogenic with said first and second strains and having the same bacteriophage binding characteristics as said first add second bacterial strains, wherein said third strain carries a DNA-encoded phage defense mechanism different from said phage defense mechanisms carried by said first and second strains.

40. A culture according to claim 38, wherein said culture is a pure culture free of non-isogenic strains.

41. A culture according to claim 38, wherein said culture is a mixed culture containing non-isogenic strains.

42. A culture according to claim 38, wherein said first and second phage defense mechanisms are carried by plasmids.

43. A culture according to claim 38, wherein said first and second phage defense mechanisms are selected from the group consisting of prevention of adsorption (Ads), restriction and modification (R/M), abortive infection (Hsp), and phage encoded resistance (Per).

44. A culture according to claim 38, wherein said first phage defense mechanism is carried by a plasmid selected from the group consisting of (a) the plasmid pTR2030, which encodes phage resistance phenotype and conjugal transfer phenotype upon expression in *lactococci*, and (b) a derivative of pTR2030, the derivative encoding the phage resistance phenotype encoded by the plasmid pTR2030 upon expression in *lactococci*.

* * * * *

UNITED STATES PATENT AND TRADEMARK OFFICE
CERTIFICATE OF CORRECTION

PATENT NO. : 5,593,885
DATED : January 14, 1997
INVENTOR(S) : Klaenhammer, et. al.

It is certified that error appears in the above-indentified patent and that said Letters Patent is hereby corrected as shown below:

Title page, item [56], under Other Publications, replace "Ericksson" with--Erickson--.

Column 11, line 56, replace "e-t al." with --et al.--

Column 22, line 6, replace "bacteria phage" with--bacteriophage--.

Column 24, line 9, replace "add" with -- and--.

Signed and Sealed this

First Day of July, 1997

Attest:

Attesting Officer

BRUCE LEHMAN

Commissioner of Patents and Trademarks